United States Patent [19]

Cronin

[11] 4,173,218

[45] Nov. 6, 1979

[54] GLOVED SPLINT FOR AN ARTHRITIC HAND

[76] Inventor: Penny S. Cronin, 7831 W. Zucca Dr., Peoria, Ariz. 85345

[21] Appl. No.: 854,130

[22] Filed: Nov. 23, 1977

[51] Int. Cl.² ............................................. A61F 5/10
[52] U.S. Cl. .................................. 128/77; 128/87 A; 128/DIG. 20
[58] Field of Search ............... 128/77, 87 A, DIG. 20

[56] References Cited

U.S. PATENT DOCUMENTS

| | | | |
|---|---|---|---|
| 1,220,476 | 3/1917 | Ujdur | 128/87 A |
| 1,817,212 | 8/1931 | Siebrandt | 128/87 A |
| 3,581,740 | 6/1971 | Sherbourne | 128/87 A |
| 3,937,215 | 2/1976 | Barthlome | 128/DIG. 20 |

FOREIGN PATENT DOCUMENTS 735700 6/1966 Canada ............................ 128/DIG. 20
270341 9/1913 Fed. Rep. of Germany ........ 128/87 A Primary Examiner—E. H. Eickholt
Attorney, Agent, or Firm—Cahill, Sutton & Thomas

[57] ABSTRACT

A gloved splint, while protecting a hand stricken with rheumatoid arthritis against painful jolts, precludes grotesque distortion of the fingers due to muscle contractions. Hinged finger splints, extending from a palm splint, permit flexing of the first finger joints in the normal manner while precluding sideways flexing of the fingers at the knuckles. A glove-like envelope, filled with a fluid, encapsulates the hand, thumb and fingers and provides a shock absorbing buffer to minimize transmission of painful blows and jolts to the hand. Insulation, vents and heating elements may be included to minimize pain through application or withdrawal of heat.

11 Claims, 6 Drawing Figures

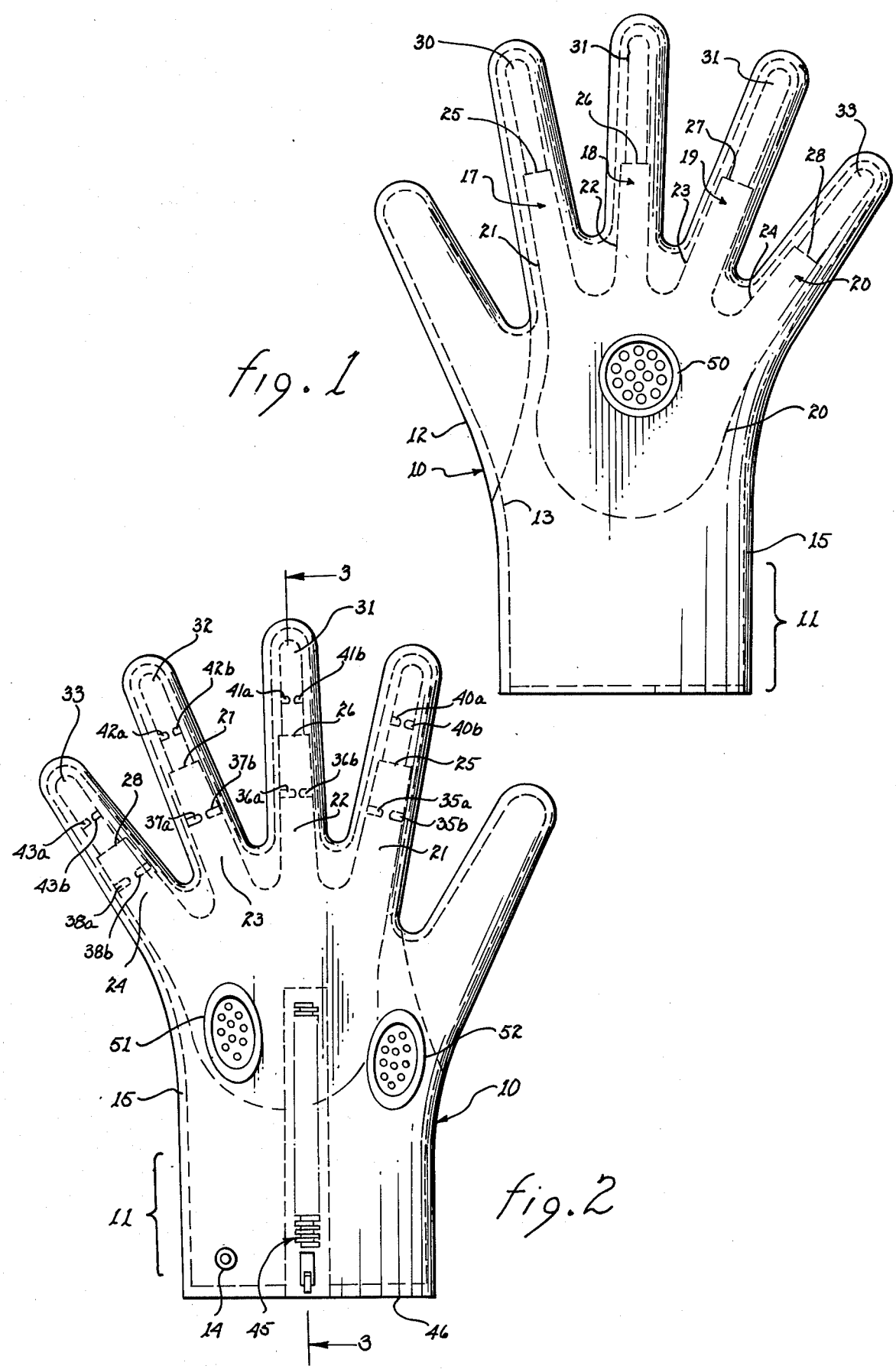

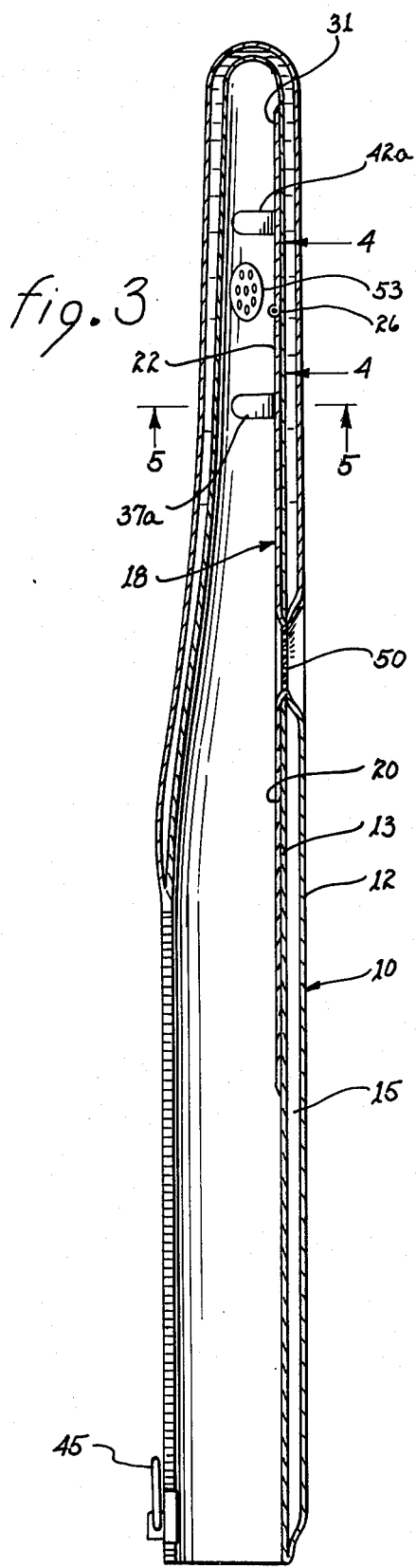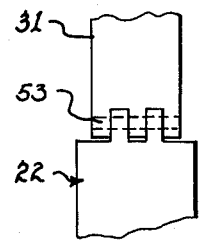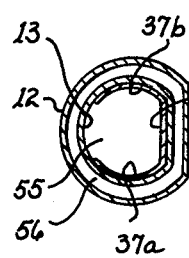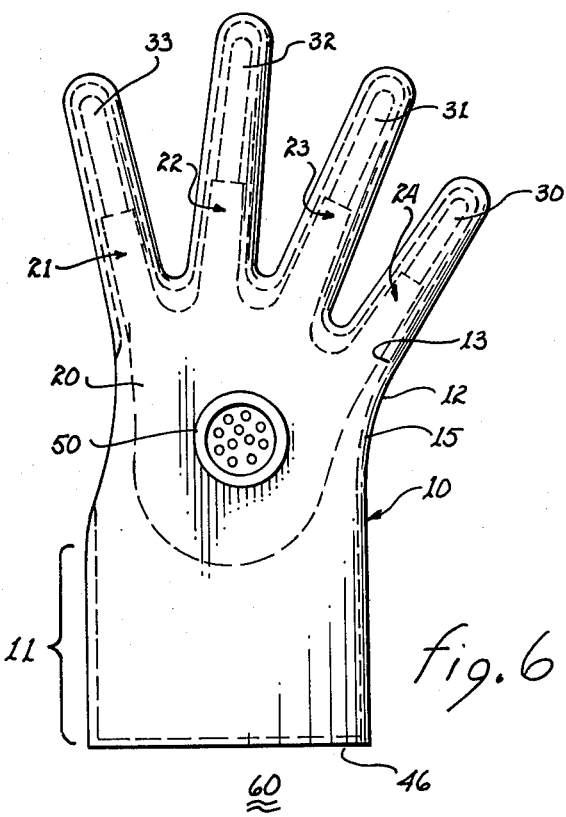

GLOVED SPLINT FOR AN ARTHRITIC HAND

The present invention relates to splints and, more particularly, to splints for use with rheumatoid arthritis stricken hands.

The word arthritis literally means inflamation of a joint. Rheumatoid arthritis is the most serious, the most painful and the most potentially crippling of the nearly 100 rheumatic diseases. Deformed hands, twisted legs, stooped shoulders and stiff elbows are often the most visible signs of the disease. It can strike suddenly and progress rapidly to an acute and seriously damaging stage.

Rheumatoid arthritis usually invades more than one joint. The joint stiffens and swells and becomes tender, eventually making full motion difficult and painful. The aching, soreness and stiffness are typically at their worst when the victim first gets up in the morning.

Rheumatoid inflamation does progressive damage inside the joint. If it is not checked by proper treatment, the following may happen. The space where two bones meet is enclosed in a capsule containing fluid. The capsule has an inner skin called the snyovil membrane. Inflamation starts here, swelling the membrane and spreading to other parts of the joint system. Outgrowths of inflamed tissue invade the cartilage surrounding the bone ends, eventually eating it away. Finally, scar tissue can form between bone ends and sometimes change to bone so that the joint becomes fused, permanently rigid and immovable.

While a joint is undergoing this destruction, muscle contractions can cause grotesque distortions. This is most apparent when the disease attacks the hands. The fingers can become skewed or drawn back and sideways, so that the hands become deformed. It is important to understand that this can happen but it can be prevented in most cases with proper treatment before it does happen.

The key to success in combating the effects of rheumatoid arthritis is a treatment program of many parts carried out faithfully over a long period of time. Such a program may include medication, exercise, rest, surgery, heat, posture correction, splints, heat and rehabilitation. The purposes of the treatment program are to relieve pain, reduce inflamation and prevent damage to the joints, prevent deformities and keep the joints movable and functioning properly.

Presently, splints, now in use to help prevent grotesque distortions of the hand, are made of plaster of paris. These are generally intended for short periods of use because of the nature of their construction. Moreover, they are inflexible and do not allow any movement of the affected body parts. Accordingly, they cannot be used repetitively by the afflicted person nor do they provide the benefits of exercising the affected joint(s). Generally, after surgery, specially constructed splints are sometimes applied to the affected joint. These splints are special purpose splints predicated upon the particular needs of the patient; since they are custom made, they are expensive.

The application or withdrawal of heat from an afflicted joint is often beneficial in alleviating the pain and discomfort attendant the joint.

A large number of United States patents have issued which describe various gloved heating devices for use with one's hands and include: U.S. Pat. Nos. 542,177, 1,970,081, 3,292,628, 3,465,120, 3,569,666, 3,621,191, 3,632,966, 3,649,966 and 4,021,640. Other patents relating to heating elements for various parts of the body include U.S. Pat. Nos. 885,112, 2,071,706 and 2,706,988.

The various devices illustrated in the above identified patents can, because of their bulk or thickness, insulate the affected part against the sharpness of any jolts and blows. However, this benefit is essentially incidental to the prime purpose of the devices.

The most common problem with arthritic hands is that of calcification of the knuckles which, by limiting flexing of the joints, results in atrophy of the finger muscles. Such atrophy, in turn, in combination with functions not fully understood, generally results in muscle contractions which skew the fingers at the knuckles. The skewing, in a regenerative manner, exacerbates the problem.

In the preferred embodiment of the present invention, a metallic splint extends across the palm and finger splints, including extensions from the palm splint, support and are attached to the first digits of the finger; thereby, the palm and finger splints preclude such skewing. Hinges, disposed in the finger splints intermediate the extensions and end segments of the finger splints permit some flexing of the fingers at the first joint to grip objects such as cups, door handles and the like. An envelope, supporting the palm and finger splints and encasing the hand, holds mineral oil or the like, which oil can serve as a heat retaining element to provide a source of warmth. In addition, the oil envelope serves the function of absorbing and buffering sharp shocks to the hand which are extremely painful. The cuff of the glove extends a sufficient distance upward the forearm to allow only limited flexing of the wrist. Air holes may be included to provide ventilation of the naturally self-heating arthritic joints.

It is therefore a primary object of the present invention to provide a reuseable removable splint for arthritic hands.

Another object of the present invention is to provide a splint which precludes lateral skewing of the fingers due to muscle contractions.

Yet another object of the present invention is to provide a hand splint for arthritic hands which accommodates limited normal finger movement while precluding lateral skewing of the fingers.

Yet another object of the present invention is to provide a splint for use during nighttime to prevent increasing non-reversible deformation of the finger joints in an arthritic hand.

A further object of the present invention is to provide a buffer for shielding an arthritic hand against the pain of jolts and bumps.

A yet further object of the present invention is to provide a means for applying heat to an arthritic hand and relieve pain.

A yet further object of the present invention is to provide a gloved splint for an arthritic hand which includes ventilation holes to preclude heat buildup of heat generated by an arthritic joint.

These and other objects of the present invention will become apparent to those skilled in the art as the description thereof proceeds.

The present invention may be described with greater specificity and clarity with reference to the following drawings, in which:

FIG. 1 is a bottom view of the present invention and illustrating the constructional features thereof;

FIG. 2 is a top view of the present invention and illustrating the constructional features thereof;

FIG. 3 is a cross-sectional view of the present invention taken along lines 3—3;

FIG. 4 is a cross-sectional view taken along lines 4—4, as shown in FIG. 3;

FIG. 5 is a cross-sectional view taken along lines 5—5, as shown in FIG. 3; and

FIG. 6 illustrates a variant of the present invention.

Referring jointly to FIGS. 1, 2 and 3, there is shown a gloved splint or hand protector incorporating the teachings of the present invention. The hand protector includes a glove 10 configured as a fingered glove to individually receive the fingers and thumb. The wrist portion 11 may terminate at the wrist or extend for a distance along the forearm. The latter configuration is preferred wherein cocking of the wrist, due to uncontrollable muscle contraction, is to be avoided. Such contraction, as discussed above, may occur conjointly with deterioration of the wrist joint due to rheumatoid arthritis. In such a case, straps, elastic or reinforcing members may be disposed upon wrist portion 11 to constrain wrist movement without rendering the wrist completely rigid.

Glove 10 includes an outer covering 12 and an inner lining 13, which, in combination, define a sealed envelope 15 for containing a liquid. As indicated in FIG. 2, access to the sealed envelope for both filling and drainage is provided through a petcock or valve 14.

A sheet of stiff, but not necessarily rigid, material is attached to inner liner 13 in proximity to the palm and defines palm splint 16 bearing against the palm of the hand. Palm splint 16 includes finger splints 17, 18, 19 and 20 having extensions 21, 22, 23 and 24 extending coincident with the respective fingers to a point approximately coincident with the first joint of each of the fingers. The terminal end of these extensions is represented by the hinge lines of hinges 25, 26, 27 and 28. The finger splints are terminated by segments 30, 31, 32 and 33 hingedly attached to segments 21, 22, 23 and 24 for supporting the remaining two digits of each finger.

The attachment of the finger splints to the fingers will be discussed with primary reference to FIG. 2. To preclude disassociation or movement of the fingers with respect to their individual finger splints, retaining means, such as tabs 35a and 25b, 36a and 36b, 37a and 37b and 38a and 38b, protrude from extensions 21, 22, 23 and 24, respectively, to partially encircle, retain or otherwise grip the first digit of each respective finger. As palm splint 20 is maintained in position with respect to the palm by the at least somewhat form-fitting glove, the palm splint is capable of little movement relative to the palm. Extensions 21-24, being an integral part of or fixedly attached to the palm splint, cannot move relative to the palm splint. By attaching the first digit of each finger to its respective extension through the above enumerated tabs, the knuckle joint of each finger is maintained essentially immobile. Further, immobility is, of course, enhanced by a tight fit of the glove. Thereby, the fingers are precluded from skewing laterally at the knuckle due to rheumatoid arthritic attendant muscle contractions.

Each of segments 30—33 is attached to one of the last two digits of each finger through retaining means or tabs 40a and 40b, 41a and 41b, 42a and 42b and, 43a and 43b, respectively. Hinges 25, 26, 27 and 28 disposed at the hinge lines corresponding to the joint between the first and second digit, permit pivotal movement of each segment with respect to its extension and independent movement of the fingertips with respect to a segment is precluded by the aforementioned tabs. Accordingly, the last two digits of each of the fingers are pivotally flexible. Such flexing permits gripping of various objects and other manipulative functions not possible were the fingers rendered totally immobile.

It is generally difficult and normally very painful to insert an arthritic hand into a conventional glove. To alleviate the discomfort of donning and removing the hand protector described herein, a zipper 45 extends from wrist opening 46 to a point generally central to the back of the hand. Thereby, access to the interior of the glove is available through a relatively large opening and insertion of one's fingers, thumb and hand is relatively easy and relatively painless. On closing of zipper 45 after one's hand has been inserted, the body of the hand protector and wrist portion are brought into snug engagement with the hand.

Arthritically inflamed joints often have a tendency to generate heat. When such heat is confined, it may exacerbate the pain. To preclude heat buildup due to the arthritic joint(s) itself or because of high ambient temperatures, a ventilator 50 may be disposed in the palm portion of glove 10. Similar ventilators 51 and 52 may be disposed in the glove adjacent the back of the hand. Additional ventilators 53, as particularly illustrated in FIG. 3, may be disposed alongside the finger portions of glove 10.

One's thumb, even though the joints may be arthritic, tends not to skew in the manner of the fingers because of the configuration and attachment points of the attendant muscles and ligaments. Moreover, the thumb joint is also of a different type and has a different function from that of the corresponding knuckle joints. For these reasons, a splint extending from palm splint 20 to support the thumb is generally not required. However, for particular purposes, an extension of the palm splint may be incorporated to support all or a portion of the thumb. Similarly, a segment of the thumb splint may be pivotally attached to accommodate at least some movement of one or another of the thumb digits.

As illustrated in FIG. 4, the hinge interconnecting the pivotal segments with their respective extensions, may be a simple hinge. Alternatively, if the splint is of plastic, the hinge section may be formed by a plurality of transverse grooves rendering flexing possible along the hinge line.

Referring to FIG. 5, there is shown a cross-section of a representative finger of the hand protector. As illustrated, interior lining 13 has attached thereto extension 22 and tabs 37a and 37b protrude from the extension into cavity 55 for receiving a finger. As envelope 15 about the finger, developed from inner liner 13 and outer covering 12, is flexible in nature, squeezing of tabs 37a and 37b will grip the partially encircled digit of the finger adjacent extension 22. Cavity 56 formed as part of envelope 15, may contain fluid, such as oil, to alleviate the sharpness of any shocks or jolts to the encased finger and the joints thereof.

FIG. 6 illustrates a variant 60 of the present invention wherein the thumb is not enclosed by a thumb portion of the glove. This version is particularly useful for persons whose fingers but not thumb are arthritic in that it allows full and unrestricted use of the thumb. It is to be understood that the constructional features of the hand protector as described with respect to FIGS. 1–5 are embodied within the variant shown in FIG. 6.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A hand protector for supporting and protecting the fingers of an arthritis stricken hand, said hand protector ... comprising in combination:
   (a) a palm splint positionable in juxtaposed relationship to the palm of the hand, said palm splint being configured to permit unrestricted normal movement of the thumb;
   (b) a finger splint extending from said palm splint for supporting each respective finger but not thumb in a non-laterally moveable relationship to the palm;
   (c) means for flexing a section of at least one of said finger splints to permit flexing of the fingers along a single axis only to control opening and closing of the fingers of the hand, said flexing means being positionally commensurate with a joint of the respective finger; and
   (d) glove means for maintaining said palm splint and said finger splints in juxtaposed relationship with the respective parts of the hand while enclosing at least the fingers and palm of the hand, said glove means including:
      i. shock absorbing means for buffering impacts and blows to the hand; and
      ii. means for opening and closing said glove means to facilitate insertion and withdrawal of the hand therefrom, whereby, said finger splints preclude lateral skewing of the fingers due to involuntary muscle contractions and yet permit mobility of the thumb and mobility of the fingers to flex.

2. The hand protector as set forth in claim 1 wherein each of said finger splints includes:
   a. an extension extending from said palm splint to the first joint of the respective finger;
   b. a section for supporting the last two digits of the respective finger; and
   c. said flexing means interconnecting said extension with said section.

3. The hand protector as set forth in claim 1 wherein said flexing means comprises hinge means for hinging each section to the respective one of said extensions, said hinge means being juxtaposed with the joint between respective digits of the finger.

4. The hand protector as set forth in claim 3 including first tab means extending from each said extension for gripping the first digit of the respective finger and second tab means extending from each said section for gripping one of the remaining digits of the respective finger.

5. The hand protector as set forth in claim 4 wherein said shock absorbing means comprises an envelope and a fluid disposed within said envelope for buffering the fingers, thumb and palm of the hand against sharp impacts and blows.

6. The hand protector as set forth in claim 5 including ventilation means disposed in said glove means for ventilating the hand.

7. The hand protector as set forth in claim 6 wherein said opening and closing means comprises zipper means for opening said glove means to aid in the insertion and withdrawal of the hand.

8. The hand protector as set forth in claim 7 including a wrist section extending from said glove means for constraining movement of the wrist joint.

9. The hand protector as set forth in claim 1 including ventilation means disposed in said glove means for ventilating the hand.

10. The hand protector as set forth in claim 1 wherein said shock absorbing means comprises an envelope and a fluid disposed within said envelope for buffering the hand against sharp impacts and blows.

11. The hand protector as set forth in claim 10 wherein said envelope comprises a common cavity extending about the hand; each of the fingers and the thumb.

* * * * *